United States Patent [19]

Erb et al.

[11] 4,279,167

[45] Jul. 21, 1981

[54] LIQUID COUPLING FOR DOPPLER SONIC FLOWMETER

[75] Inventors: Tom L. Erb; Wendell D. Miller, both of Austin, Tex.

[73] Assignee: Ramsey Engineering Company, St. Paul, Minn.

[21] Appl. No.: 80,730

[22] Filed: Oct. 1, 1979

[51] Int. Cl.³ .................. G01F 1/66; G01N 29/02
[52] U.S. Cl. .................. 73/861.25; 73/644
[58] Field of Search ............ 73/644, 861.25, 861.26, 73/861.27; 310/334, 336

[56] References Cited

U.S. PATENT DOCUMENTS

| | | | |
|---|---|---|---|
| 2,592,134 | 4/1952 | Firestone | 310/336 X |
| 3,798,961 | 3/1974 | Flambard et al. | 73/644 |
| 3,913,386 | 10/1975 | Saglio | 73/644 |
| 4,059,098 | 11/1977 | Murdock | 73/644 X |

FOREIGN PATENT DOCUMENTS 925541  5/1963  United Kingdom .................. 73/861.25

*Primary Examiner*—Charles A. Ruehl
*Attorney, Agent, or Firm*—William C. Norvell, Jr

[57] ABSTRACT

A coupling device for attachment of a sonic doppler flowmeter to pipes or conduits is shown and described. In this coupling, a temperature compensated liquid wedge is used to couple the transducer to the wall of the pipe or conduit, and means are shown and described for eliminating bubbles from the liquid wedge region.

23 Claims, 6 Drawing Figures

LIQUID COUPLING FOR DOPPLER SONIC FLOWMETER

BACKGROUND OF THE INVENTION

1. Field of the Invention

This invention relates to the measurement of fluids flowing in pipes or conduits by use of the doppler sonic flow measurement technique. In such measurements, sound waves are transmitted through the walls of a pipe, and are received from the pipe again through the walls. A reliable coupling between the sonic transducers and the pipe walls must be provided for efficient transmission and reception of sound. The present invention provides an improved liquid coupling for sound transmission and reception to and from the walls of a pipe. This coupling provides temperature compensation and the capability of bubble elimination.

2. Description of the Prior Art

In ultrasonic flowmeters, it has been common to attach the transducers to the walls of a pipe by means of epoxy resins, grease, and liquid couplings which utilize coupling wedges of different materials.

Doppler sonic flowmeters operate by directing a transmitted beam of sound energy into a pipe within which the fluid flow is being measured. The sonic energy in doppler systems is scattered from the macroscopic or microscopic bubbles, particles and/or eddy currents in the moving fluid. A sonic receiver detects the scattered energy and provides an electrical signal representative of the scattered energy to an electronic detection unit which in turn calculates the flow. The calculation of the flow is based upon the doppler frequency shift between the transmitted sonic wave and the received sonic wave. In some applications, the same sonic transducer is used for both transmitting and receiving, while in other systems separate transducers are used for transmission and reception.

It is essential in such doppler systems that the sonic transmit and/or receiver sensor be placed at an angle with respect to the direction of fluid flow. Placement of the sensors directly perpendicular to the direction of flow does not provide a meaningful measurement. Typically, a wedge of material is placed between the transducer and the pipe carrying the fluid whose velocity is being measured to provide the desired angle between the sensor and the fluid flow.

In such systems, the flow indication is inversely proportional to the velocity of sound through the wedge material. Consequently, it is desirable that the wedge material have a low sound transmission-temperature coefficient to ensure the desired flow indication accuracy over a given temperature range. In systems which employ electronic compensation of the temperature effects, it is necessary that the sound transmission-temperature coefficient of the wedge material be accurately known.

Conventional systems utilizing wedges have employed hard materials, such as steel, aluminum and glass. These materials have fairly low sound transmission-temperature coefficients. However, such materials also exhibit a very high velocity of sound propagation, whereas the material between the wedge and the pipe, such as grease and epoxy adhesives, typically exhibit much lower velocity of sound propagation values. Consequently, there is a very high degree of refraction and a very large acoustic impedance mismatch between this type of wedge and such interface materials causing most of the signal to be lost due to reflection.

In systems which employ wedges fabricated from plastic or polyester materials, sound transmission temperature coefficients in the order of 0.1 percent per degree centigrade to 0.2 percent per degree centigrade are common. Such coefficients require electronic temperature compensation for accurate fluid flow measurements.

As used in this specification, the term sound transmission temperature coefficient is defined as the change of sound transmission velocity with respect to temperature, typically expressed as a percentage per degree centigrade.

Another problem associated with conventional solid wedge materials is that of physically coupling the said wedges to the pipes which carry the fluid flow being measured. Conventionally, coupling has been achieved by the use of epoxy adhesives or coupling greases. Both epoxy adhesives and coupling greases, however, cause serious technical problems due to the presence of air bubbles or gas trapped in such materials. Such air bubbles, even at microscopic levels, detrimentally effect the accuracy of the doppler sound measurement. A high level of entrapped air bubbles present in the coupling can even cause a complete loss of measurement capability of the sonic doppler flowmeter. Further, it is not always possible to determine whether the flowmeter is operating at its full accuracy because of the uncertainty of the bubble formation in the coupling.

In the prior art use of solid wedge materials in combination with epoxy or grease couplings, there has developed yet another problem associated with the use of such flowmeters in the field. In field use, it is not always possible to achieve uniform mixtures of the epoxy or grease materials, or to achieve the desired bubble free condition of such materials. In the case of epoxy resins, the mere aging of the resins typically results in a change in the sound transmission characteristics of such resins, which change may require further calibration to insure the desired measurement accuracy.

The use of solid wedges within fluid couplings to compensate for temperature effects on the velocity of sound propagation is known in the art. For example, U.S. Pat. No. 3,913,386 employes a liquid coupling which forms the wedge between the ultrasonic flowmeter transducer element and the conduit through which the flow is being measured. As shown therein, a wedge of material having a sound transmission temperature coefficient which is opposed to that of the liquid is placed in the path of propagation of the sonic energy. In this technique, the opposite sound transmission temperature coefficients of the two different materials are used to compensate for the sound transmission temperature coefficient which otherwise is present in the fluid alone. In this system, however, substantial attenuation of the sonic energy is experienced because each interface between the fluid and the solid wedge material produces a substantial attenuation loss.

Furthermore, the system disclosed in U.S. Pat. No. 3,913,386 is utilized for ultrasonic testing of materials, such as metallic welds. The disclosure relates only to a method of temperature compensation for the angle of refraction of the sonic beam by use of two materials, one solid and one liquid, between the emitter of the sonic beam and the material to be measured. Thus, this disclosure relates to a compensation method which utilizes two wedges of different materials and physical states, and does not employ a single wedge of uniform material with a controllable constant temperature coefficient. This disclosed system is not analogous to doppler measurement techniques. Rather, it relates to a measurement which relies upon refraction and, thus, its purpose and application are entirely different from the apparatus and method of the present invention.

SUMMARY OF THE INVENTION

A liquid wedge coupling is provided in the present invention between the ultrasonic transmitter and/or receiver transducer and the pipe, the fluid flow through which is being measured by doppler sonic flowmeter methods. The liquid wedge of the present invention provides solutions to many of the problems encountered in conventional grease and epoxy sonic transmission coupling systems. By the use of a liquid wedge, bubbles no longer are a problem in the present invention because they travel up through the liquid and out of the region of the wedge. Therefore, complete assurance of bubble free wedges is accomplished.

The present invention contemplates the use of a liquid wedge made up of a mixture of a plurality of liquids, with each liquid having a different sound transmission temperature coefficient. The coefficients of the various liquids are proportioned so that the sound transmission characteristics through the liquid wedge are compensated with respect to temperature changes of the wedge. For example, the plurality of liquids can exhibit positive and negative sound transmission temperature coefficients so that the composite liquid wedge exhibits a substantial zero sound transmission temperature coefficient.

A single medium is provided in the present invention between the transmitting and receiving transducers of a doppler flow measurement system. Consequently, sonic energy attenuation produced by a plurality of coupling interfaces is substantially eliminated by the present invention. The invention also contemplates the use of sonically absorptive liquids for the wedge to control and reduce certain standing wave problems which often occur in doppler flow measurement. In addition, there is provided a plurality of fluid passages which, when used with a hypodermic syringe, provide for the capability of insertion of fluid into the coupling region and provide the capability of removal of air from the coupling region.

OBJECTS OF THE INVENTION

It is an object of the present invention to provide an improved coupling between a transducer and pipe in a doppler sonic flow measurement apparatus and method.

It is another object of the present invention to provide a liquid coupling wedge which is free of bubbles and other impurities which may degradate the performance and accuracy of a doppler sonic flowmeter apparatus and method.

It is a further object of the present invention to provide a liquid coupling which is temperature compensated by the use of a plurality of fluids with different sound transmission temperature coefficients.

These and other objects are achieved by the apparatus and method of the present invention.

DETAILED DESCRIPTION OF THE INVENTION

Figure 1:
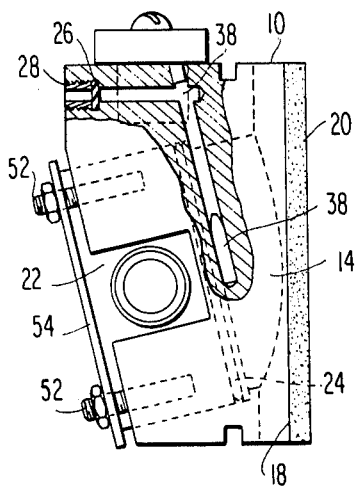
In FIG. 1, there is shown a side view of a liquid wedge coupling in accordance with the present invention.

FIGS. 1 through 6 show various views of the coupling device of the present invention, designated generally by reference numeral 10, which is used for coupling a doppler sonic flowmeter to a conduit or pipe 12. The velocity of the fluid flowing within conduit or pipe 12 is measured by the doppler sonic flowmeter. In order for the flow measurements to be accurate, it is essential that a sonic transmitter, such as a transducer 22, be disposed at an angle with respect to the direction of flow of the fluid within pipe 12, as shown best in FIG. 2. A wedge-shaped cavity, designated by reference numeral 14, is placed between transducer 22 and conduit 12.

Figure 2:
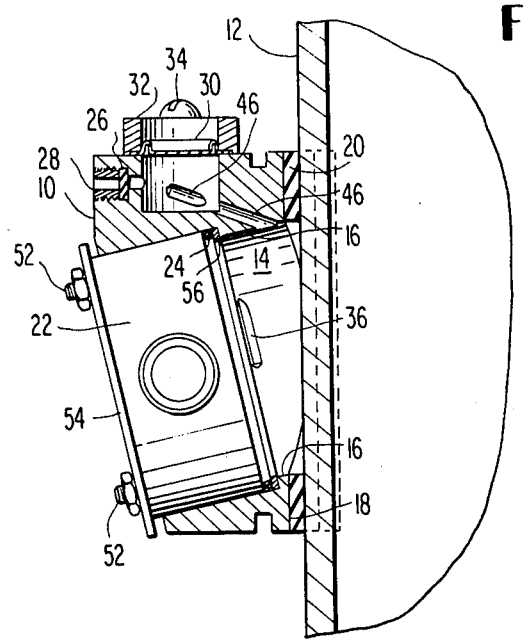
FIG. 2 shows another side view partly in cross-section of the coupling of the present invention affixed to a conduit or pipe whose fluid flow rate is to be measured using doppler sonic techniques.

Referring now to FIGS. 1 and 2, a wedge-shaped cavity 14 contains a coupling agent or fluid which transmits the sonic energy from transducer 22 to conduit 12. Coupling device 10 includes a seal means 20, which is used to provide a liquid-tight connection to the outer surface of conduit 12. Seal means 20 may be any suitable compressible gasket material, such as rubber or plastic. Transducer 22 is pressed into the body of coupling device 10 by means of retaining screws 52 and an associated retaining plate 54. Associated with transducer 22 is an O-ring 24 of any suitable type which provides a fluid seal between transducer 22 and coupling device 10.

Figure 6:
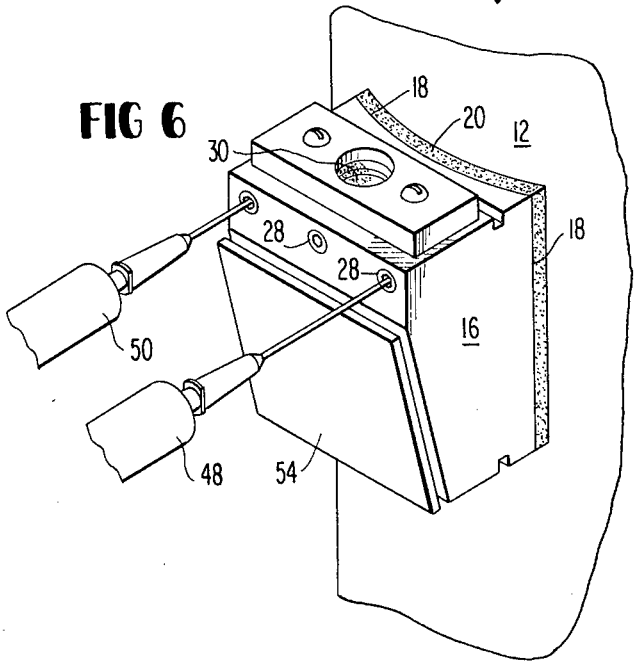
FIG. 6 shows the coupling in rear perspective attached to a pipe or conduit with hypodermic needles connected, respectively, for inserting fluid into the coupling region or cavity.

In order to insert the liquid for the liquid wedge into the wedge-shaped cavity, it is necessary to provide means for filling cavity 14. As shown in FIG. 1, one such filling means comprises a side fill tube 38, which is constructed by drilling passages in the body of the coupling device 10. FIG. 1 shows the fill tube 38 entering the side of cavity 14. Associated with fill tube 38 is a flexible membrane 26 and a retaining hollow set screw 28. Membrane 26 is constructed so that it provides a seal for the fluid contained within tube 38 and the environment. In this embodiment, as depicted in FIG. 6, a hypodermic needle 48 may be used to insert fluid into cavity 14 by inserting the needle of the hypodermic needle through membrane 26. Similarly, a second hypodermic needle 50 may be used to remove air from cavity 14 through another fill tube 36 and associated membrane 26, as depicted in FIG. 6.

Figure 4:
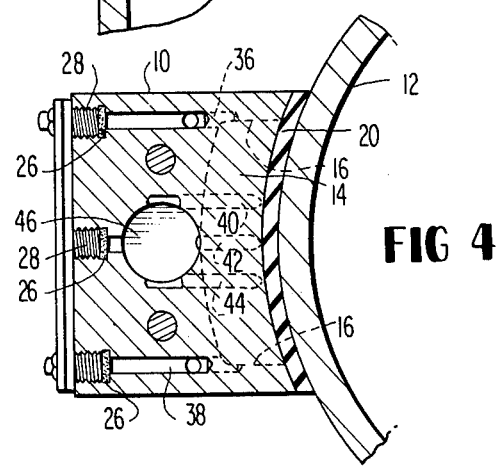
FIG. 4 shows a top cross-sectional view of the liquid wedge coupling with the various channels for insertion of liquid into the coupling.
Figure 5:
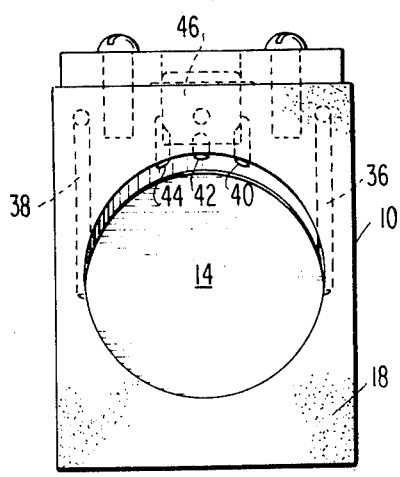
FIG. 5 shows the front view of the coupling.

In order to achieve complete filling of cavity 14 with the liquid coupling agent, it is necessary to provide a plurality of fill tubes which allow for the insertion of the liquid and the removal of trapped air regardless of how the coupling device 10 is oriented with respect to the vertical plane. In FIGS. 4 and 5, there are shown fill tubes 36, 38, 40, 42 and 44. As can be seen in FIG 2, if conduit 12 is oriented to lie in the vertical plane, fill tubes 40, 42 and 44 appear at the top of the cavity 14, and therefore are available for removal of trapped air, which appears at the top of cavity 14 in such an orientation. If conduit 12 lies in horizontal plane, however, as indicated in FIG. 4, fill tube 36 provides the uppermost connection to the cavity 14 and the environment. In such an orientation, liquid may be inserted into the lower fill tubes such as 38 or 42 and air removed by fill tube 36. Fill tubes 40, 42 and 44 are all connected to a central filling cavity, designated by reference numeral 46, which is connected in turn to a single membrane 26 and associated set screw 28 to seal these fill tubes from the environment.

As illustrated in FIG. 6, hypodermic needles 48 and 50 interchangeably may be used to remove trapped air from cavity 14 and to insert the coupling agent fluid into cavity 14. By insertion of the hypodermic needles into the various flexible membranes 26, substantially all of the air may be removed from the cavity 14. Further, any air which may remain, will rise to the upper portion of the cavity 14 of coupling device 10 and into the central filling cavity 46 associated with tubes 40, 42 and 44 or into the more elevated of tubes 36 and 38. By this arrangement, it is therefore possible to remove all air from the wedge-shaped cavity 14 and to provide a uniform homogenious liquid coupling between sonic transducer 22 and the wall 12 of the conduit which carries the fluid whose velocity is to be measured by the doppler flow technique.

Figure 3:
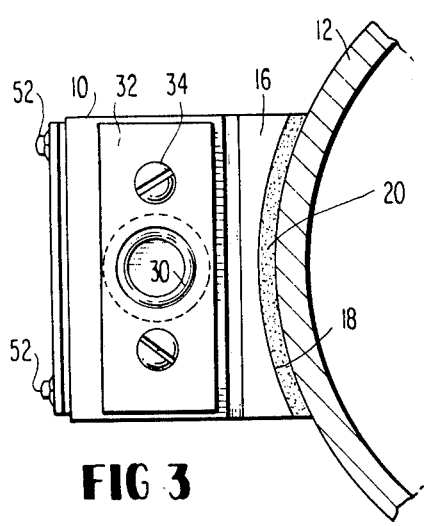
In FIG. 3, there is shown a top view of the coupling affixed to a conduit or pipe.

Once cavity 14, the fill tubes 36, 38, 40, 42 and 44, and the central filling cavity 46 are filled with coupling fluid, it is necessary to provide for the temperature expansion of the fluid. This expansion is accomplished by the use of an expansion means or membrane 30. Membrane 30 is retained in place on the central filling cavity 46 by means of a plate retainer 32 and retaining screws 34, as shown in FIGS. 2, 3 and 6.

As can be seen in FIG. 6, hypodermic needle 48 or hypodermic needle 50 may comprise a filling means, whereas the other hypodermic needle may comprise a means for trapped air release. Similarly, either needle 48 or 50 may be inserted into the central filling cavity 46 by way of the centrally located membrane 26.

The liquid-tight wedge shaped cavity 14 may obviously be constructed in any suitable geometric shape. In the present embodiment, the walls 16 of the liquid-tight cavity 14 are partially cylindrical in shape, but other shapes may be appropriate and are contemplated by the present invention. Walls 16 have end or shaped portions 18. Shaped portions 18 are configured to conform to the conduit or pipe 12 to which coupling device 10 is attached. It is apparent that the attachment may be of any suitable geometric shape which fits the shape of the walls of the conduit 12 to which the coupling device 10 is attached. The attachment of coupling device 10 to the pipe wall 12 is merely by pressure. Coupling device 10 may be suitably attached to conduit or pipe 12 by straps or other means to hold the coupling device 10 against the pipe 12. It should be understood that the present invention contemplates any suitable method and apparatus for attaching the coupling device 10 to the wall of conduit or pipe 12, irrespective of the shape of conduit or pipe 12.

The fluid used for the liquid coupling defined by cavity 14 is composed of a mixture of two or more different mixable liquids which, when mixed effectively, control the sound transmission temperature coefficient of the liquid wedge formed thereby. If, for example, one liquid with a positive sound transmission temperature coefficient is mixed with another liquid having a negative sound transmission temperature coefficient, it is possible, using the method and apparatus of the present invention, to obtain a liquid with a nearly constant sound transmission temperature coefficient. By this technique, the speed of sound in the liquid wedge remains nearly constant regardless of temperature. Further, it is possible in the apparatus and method of the present invention to achieve any desired sound transmission temperature coefficient for the liquid wedge by appropriate control of the ratios of two or more mixable liquids. It further should be noted that it is also possible to utilize liquids for the liquid wedge which have sonic absorption capabilities. By use of sonically absorptive liquids, certain standing wave problems associated with doppler sound measurement may be eliminated by the liquid wedge itself.

In doppler sound measurement, any air bubbles which exist in the region of the coupling typically adversely affect the accuracy and performance of the fluid flow measurement. Even microscopic air bubbles in the coupling material can cause substantial errors in performance. Therefore, it is essential that the coupling between the sonic transducer and the fluid flow be made without entrapping air bubbles, irrespective of size. If there are any entrapped air bubbles present in the coupling, deterioration in performance accuracy is highly probable and loss of measurement capability is possible for the doppler sonic flowmeter.

These problems are eliminated by the method and apparatus of the present invention. By the use of a liquid wedge together with the hypodermic syringe filling technique described above, the present invention provides liquid wedge coupling without bubbles because there are no bubbles in the wedge-shaped cavity 14. The elimination of entrapped air bubbles in the coupling area is assured because any bubbles naturally (because of gravity) float out of the coupling area and into the fill tubes 36 through 44 or the central filling cavity 46. Thus, the coupling device 10 with multiple fill tubes and a technique for convenient insertion of the coupling fluid into the wedge-shaped coupling region provides for a sonic coupling without air bubbles.

As can be seen in FIG. 6, the use of hypodermic needles 48 and 50 for inserting fluid and removing air bubbles is another advantageous aspect of the present invention. Hypodermic needles have been found to be particularly advantageous in the present invention because they provide for a convenient method of filling even under adverse industrial environments. By the system herein disclosed, it is possible to provide excellent sonic couplings to pipes or conduits under adverse industrial conditions without the risk of air bubbles or dirt contamination which would otherwise degradate or destroy the performance of a doppler sonic flowmeter system. By ensuring that bubbles float out of the coupling area, substantially optimum coupling is assured by the present invention.

As explained above, by mixing positive and negative sound transmission temperature coefficient fluids, a substantially constant sound transmission temperature coefficient for the liquid may be achieved by the method and apparatus of the present invention. This is important because it substantially eliminates the electronic compensation required by doppler sonic flowmeters. using conventional coupling apparatus and methods. In some instances, electronic compensation may be entirely eliminated by the present invention where the temperature of the liquid wedge is maintained within the limits where the sound transmission temperature coefficient of the liquid coupling wedge is substantially constant.

One suitable mixture for the liquid wedge is a mixture of water ($H_2O$), which has a positive sound transmission temperature coefficient, with a liquid having a negative sound transmission temperature coefficient, such as ethylene glycol or glycerine. It should be understood that the present invention encompasses any suitable mixture for the liquid wedge.

While there have been shown and described what are at present considered to be preferred embodiments of the present invention, modifications thereto will readily occur to those skilled in the art. It is not desired, therefore, that the invention be limited to the specific arrangements shown and described, and it is intended to cover in the appended claims all such modifications as fall within the true spirit and scope of the invention.

What is claimed is:

1. A sonic coupling between a sonic transducer and a wall of a conduit comprising:
    (a) means for forming a liquid-tight cavity between said sonic transducer and said wall of said conduit;
    (b) a liquid having a substantially constant sound transmission temperature coefficient over a desired temperature range, said liquid substantially filling said means for forming a liquid-tight cavity;
    (c) membrane means which normally seals said means for forming a liquid-tight cavity from the environment outside said means for forming a liquid-tight cavity; and
    (d) hypodermic needle means for selectively adding said liquid to said means for forming a liquid-tight cavity and for removing gas from said means for forming a liquid-tight cavity by passing a portion of said hypodermic needle means through said membrane.

2. The sonic coupling of claim 1, wherein said liquid is a mixture of at least two component liquids, at least one of said component liquids having a sound transmission temperature coefficient opposite to the sound transmission temperature coefficients of the other component liquids, said component liquids mixed in proportions so that the sound transmission temperature coefficient of said liquid is substantially constant over a desired temperature range.

3. The sonic coupling of claim 1, wherein said means for forming a liquid-tight cavity comprises:
    cavity means having a shaped-portion which substantially conforms to said wall of said conduit; and
    seal means arranged between said shaped-portion and said wall for providing a liquid-tight seal between said cavity means and said conduit.

4. The sonic coupling of claim 3, wherein said transducer is effectively sonicly connected to said liquid to said cavity means.

5. The sonic coupling of claim 3, wherein said seal means is resilient material attached to said shaped-portion for providing a seal when said cavity means is in compression with said conduit.

6. The sonic coupling of claim 1, further comprising expansion means within a portion of said means for forming a liquid-tight cavity for providing for expansion and contraction of the volume of said means for forming a liquid-tight cavity as the volume of said liquid changes with temperature.

7. The sonic coupling of claim 6, wherein said expansion means is a membrane.

8. The sonic coupling of claim 1, wherein said means for forming a liquid-tight cavity is wedge shaped.

9. The sonic coupling of claim 1, wherein said liquid absorbs sonic standing waves.

10. In a sonic flowmeter apparatus employing a transducer to measure the flow of a media in a conduit, an improved transducer means coupling comprising:
    (a) means for forming a liquid-tight cavity between a wall of said conduit and said transducer;
    (b) a liquid having a substantially constant sound transmission temperature coefficient filling said means for forming a liquid-tight cavity; and
    (c) means for inserting said liquid into said means for forming a liquid-tight cavity including membrane means which normally seals said cavity from the environment outside said cavity and hypodermic needle means for selectively adding said liquid to said means for forming a liquid-tight cavity or for removing gas from said means for forming a liquid-tight cavity by passing a portion of said hypodermic needle means through said membrane means.

11. The apparatus of claim 10, wherein said liquid is a mixture of component liquids having opposite sound transmission temperature coefficients, which component liquids are mixed in proportions so that the combined sound transmission temperature coefficient of said liquid is substantially the temperature range of said media.

12. The apparatus of claim 11, wherein said selected temperature range is substantially the temperature range of said media.

13. The apparatus of claim 10, wherein said liquid is a mixture of water having a positive sound transmission temperature coefficient and a liquid having a negative sound transmission temperature coefficient.

14. The apparatus of claim 10, wherein said means for forming a liquid-tight cavity comprises:
    a cavity having a shaped-portion which substantially conforms to said wall of said conduit; and
    seal means disposed between said shaped-portion and said wall for providing a liquid-tight seal between said cavity and said conduit.

15. The apparatus of claim 14, wherein said cavity is connected to said transducer means and transmits sound between said transducer means and said liquid filling said cavity.

16. The apparatus of claim 14, wherein said seal means is a resilient material attached to said shaped-portion and forms a seal when said cavity is pressed against said wall of said conduit.

17. The apparatus of claim 10, further comprising expansion means within a wall of said means for forming a liquid-tight cavity for providing for expansion and contraction of the volume of said means for forming a liquid-tight cavity as the volume of said liquid changes with temperature.

18. The apparatus of claim 17, wherein said expansion means is a flexible membrane mounted in said wall.

19. A method of coupling transducer means of a sonic flowmeter apparatus to a conduit within which the flow of a media is to be measured, said method comprising the steps of:
    (a) providing a liquid-tight cavity between a wall of said conduit and said transducer means; and
    (b) substantially filling said liquid-tight cavity with a liquid having a substantially constant sound transmission temperature coefficient by inserting a hypodermic needle through membrane means provided in a wall of said liquid-tight cavity.

20. The method of claim 19, wherein said liquid is a mixture of component liquids having opposite sound transmission temperature coefficients, which component liquids are mixed in proportions so that the combined sound transmission temperature coefficient of said liquid is substantially constant over a selected temperature range.

21. The method of claim 19, further including the step of providing for the escape of air from said cavity during the step of filling said liquid-tight cavity with fluid.

22. The method of claim 21 wherein said step of providing for the escape of air from said cavity is accomplished by inserting a hypodermic needle through a membrane providing in a wall of said liquid-tight cavity.

23. The method in accordance with claim 19, wherein said liquid-tight cavity is wedge shaped.

* * * * *